United States Patent [19]
Miller

[11] 3,963,446
[45] June 15, 1976

[54] APPARATUS FOR CONDUCTING A CONTINUOUS CHEMICAL REACTION WITH INTERNAL RECYCLE

[75] Inventor: Donald Nelson Miller, Wilmington, Del.

[73] Assignee: E. I. Du Pont de Nemours and Company, Wilmington, Del.

[22] Filed: Jan. 14, 1975

[21] Appl. No.: 540,845

Related U.S. Application Data

[62] Division of Ser. No. 442,908, Feb. 15, 1974.

[52] U.S. Cl. ........................... 23/288 A; 23/253 A; 23/283; 23/288 E; 203/1; 203/DIG. 6; 202/181
[51] Int. Cl.² ........................ B01J 8/00; B01D 3/42
[58] Field of Search ............ 23/288 A, 283, 253 A, 23/288 E; 202/181; 203/DIG. 6, 1

[56] References Cited
UNITED STATES PATENTS 3,700,566  10/1972  Bellinger et al. .................... 203/1

OTHER PUBLICATIONS

Hengstebeck; J., "Distillation, Principles and Design Procedures," Reinhold Publ. Co. N.Y. (1961), pp. 18–21, pp. 281–285.

Pyle, edited by C. H. Nielsen, "Distillation in Practice," Rheinhold Publ. Co., N.Y., (1956), pp. 22–24.

*Primary Examiner*—Morris O. Wolk
*Assistant Examiner*—Barry I. Hollander

[57] ABSTRACT

Apparatus for conducting a continuous, pressurized liquid-state reaction while maintaining internal recycle. The apparatus has a perforated barrier plate which separates a reaction zone from a reboiler zone and has a by-pass conduit which connects these two zones. Control devices maintain the liquid levels in the reaction and reboiler zones. A heater in the reboiler zone evolves vapors in that zone, which vapors return to the reaction zone through the perforated barrier plate.

3 Claims, 1 Drawing Figure

U.S. Patent June 15, 1976 3,963,446
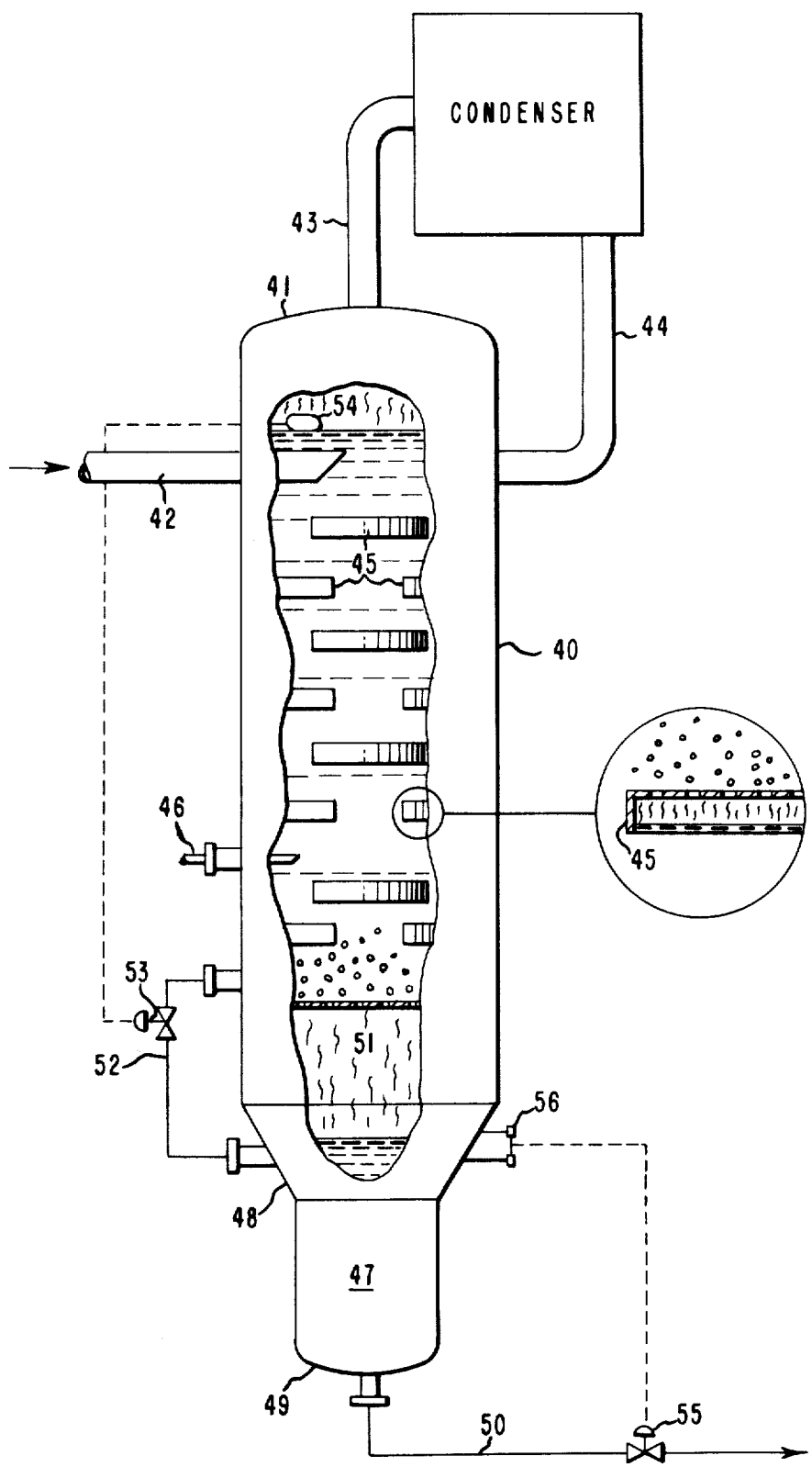

3,963,446

APPARATUS FOR CONDUCTING A CONTINUOUS CHEMICAL REACTION WITH INTERNAL RECYCLE

CROSS REFERENCE TO RELATED APPLICATIONS

This application is a divisional of application Ser. No. 442,908, filed Feb. 15, 1974.

BACKGROUND OF THE INVENTION

This invention relates to apparatus for conducting a continuous chemical reaction with internal recycle and, more particularly, relates to apparatus useful for the esterexchange conversion of ethylene glycol-degraded polyethylene terephthalate.

High molecular weight polyesters of terephthalic acid and aliphatic dihydric alcohols are well known in the art. Polyethylene terephthalate is a commercially preferred polyester of this class due to its exceptional physical and chemical properties.

Polyethylene terephthalate is typically prepared by contacting an organic ester of terephthalic acid, such as dimethyl terephthalate, with ethylene glycol in the presence of an ester exchange catalyst to form dihydroxyethyl terephthalate monomer, and then polymerizing the monomer to high molecular weight using condensation polymerization techniques. Details of this process are disclosed in U.S. Pat. No. 2,465,319 to Whinfield and Dickson. Various inert additives, such as slip additives, are generally added during the process to adapt the polyester for its intended commercial use as a packaging film, fiber, electrical insulator, molded article, etc.

Considerable waste is generated as the polyester is manufactured into commercial form. For instance, edge trim, slitting trim, and reject material is accumulated as polyethylene terephthalate is extruded, biaxially stretched, and slit into film widths desired by customer industries. The industry has proposed a variety of processes for reclaiming these wastes in order to conserve resources and eliminate ecological problems associated with waste disposal.

One proposal has been to (1) degrade the polyester wastes with the glycol used in making the polyester to prepare dihydroxyalkyl/terephthalate, followed by (2) reacting the degraded wastes with a monohydric alcohol to convert the terephthalic acid values to dialkyl terephthalate. The dialkyl terephthalate, when recovered, would be recycled to prepare fresh polyester.

East German Pat. No. 69,500, for instance, discloses a waste recovery procedure wherein (1) polyethylene terephthalate is degraded with ethylene glycol, and (2) the degraded product is reacted with methanol in the presence of an ester exchange catalyst under superatmospheric pressure and at an elevated temperature to prepared solution containing dimethyl terephthalate. After the release of the superatmospheric pressure, the solution is cooled to crystallize dimethyl terephthalate which is then recovered using a centrifuge.

Although the glycol-degradation step disclosed in the German patent is satisfactory, the methanol ester exchange and recovery steps are not readily adapted for continuous commercial operation. Cooling of the solution to crystallize dimethyl terephthalate causes a substantial heat loss since excess methanol contained in the solution must be reheated for recycle. Also, the recovered dimethyl terephthalate contains occluded contaminants which detract from the properties of polyester made therefrom, inert additives present in the wastes, and some of the ester exchange catalyst. Presence of these materials complicates quality control in manufacture of polyester made from recovered dimethyl terephthalate. Moreover crystallization recovery techniques are better adapted to a batch process than the more desirable continuous process.

Thus, there is a need for an improved process and apparatus for preparing dialkyl terephthalate from glycol-degraded polyester wastes. Especially desirable is apparatus which can readily be integrated in a continuous commercial polyester waste recovery operation.

SUMMARY OF THE INVENTION

Accordingly, the present invention provides apparatus for conducting a continuous chemical reaction in the liquid state under pressure, while maintaining internal recycle of the more volatile liquid present. The apparatus comprises:

1. a closed reaction vessel with an upper reaction zone and a lower reboiler zone, said reaction zone having an entrance port for reactants and said reboiler zone having an exit port for reaction product;
2. a perforated barrier plate mounted in the reaction vessel to separate said reaction zone from said reboiler zone;
3. liquid level sensing means mounted in said reaction zone to detect the level of liquid reactants therein;
4. a conduit by-passing the perforated barrier plate to transport liquid from said reaction zone to said reboiler zone;
5. control means mounted in said by-pass conduit responsive to said reaction zone liquid level sensing means to maintain liquid in the reaction zone at a predetermined level;
6. liquid level sensing means mounted in the reboiler zone to detect the level of liquid therein;
7. a conduit to remove liquid product from the reboiler zone having mounted therein control means responsive to said reboiler liquid level sensing means, maintaining liquid in the reboiler zone at a predetermined level; and
8. heating means to maintain liquid in said reboiler zone at a higher temperature than liquid in said reaction zone.

DESCRIPTION OF THE DRAWING

The drawing is a vertical view, in partial section, of a chemical reactor useful for converting glycol-degraded waste to dialkyl terephthalate.

DESCRIPTION OF THE PREFERRED EMBODIMENTS

The reaction zone is a right cylinder section of the closed vessel, 40, and is provided with an entrance line, 42, mounted in the upper portion thereof for the introduction of reactants, and an injection nozzle, 46, mounted in the lower portion thereof for the introduction of catalyst sequestering agent. A hemispherical top, 41, is provided having a port for the continuous removal of vapors, primarily methanol, from the vessel. The vapors are continuously fed to a condensor, COND, by line 43, wherein the vapors are condensed. Liquid from the condensor is continuously returned to the vessel by line 44.

A purge line (not shown) is installed in condenser vapor line 43. The purge line has a pressure relief valve to control column temperature and pressure, providing smooth continuous operation in the case of feed fluctuations and preventing undue buildup of inert gases in the condenser recycle loop and vapor space above the reaction zone. A typical control valve setting is 500 psi. The column pressure, and temperature, equilibrates at the control valve setting, resulting in a small flow of vapors in the purge line when the feed fluctuates or inerts accumulate.

Perforated trays, 45, baffles, or other structures having a suitable design to impede downward flow of reactants and to promote liquid-vapor contact, without being plugged by solids present in the glycol-degraded wastes, are mounted in the reaction zone. Preferred perforated trays, shown in the enlargement, have a lip which extends below the tray, and the holes are sized small enough to impede downward flow of liquids through the holes but large enough to permit upward flow and bubbling of vapors through the holes. In this design the lip serves to trap vapor beneath the tray, restricting the upward flow of vapor to passage through the perforated tray. Trays having holes of about 0.25 inch diameter on a 1.25 inch triangular spacing are suitable under the operating conditions described hereinafter for the preparation of dimethyl terephthalate.

The reboiler zone forms the bottom section of the closed vessel. This zone is constructed to have a large surface area for transfer of heat into liquid contained therein, and to contain a limited volume of liquid so that residence time in the reboiler zone is short enough to minimize reactions between dimethyl terephthalate and other constituents of the liquid.

In the embodiment shown in the drawing, the reboiler zone is defined by a right cylinder section 47 of smaller diameter than the reaction zone wall 40, a truncated conical section 48 which connects the walls of the reaction and reboiler zones, and a hemispherical bottom section 49 having an exit port which communicates with line 50 for removal of product from the closed vessel. The reboiler zone is internally heated by immersed heated tubes (not shown).

A perforated barrier plate 51 is mounted in the closed vessel below the lowest tray 45 and extending across the entire cross-section area of the vessel. This barrier plate divides the vessel into the reaction and reboiler zone. The perforations are sized small enough to prevent any substantial liquid flow through the barrier plate, but large enough to permit upward flow of vapors from the reboiler to the reaction zone. A barrier plate having 0.25 inch diameter holes on a 2.25 inch triangular spacing is suitable under the operating conditions described herein for the preparation of dimethyl terephthalate.

A by-pass conduit, 52, is provided which communicates with an exit port located in the reaction zone above the barrier plate and with an entrance port located below the liquid level in the reboiler zone. Mounted in the by-pass line is a control valve, 53, responsive to a float, 54, mounted in the reaction zone to maintain a constant liquid level in the reaction zone. The by-pass line presents a sufficient liquid head to prevent reverse flow of liquids from the reboiler to the reaction zone. If necessary, a pump or other means can be installed in the by-pass line to ensure that liquid only flows from the reaction zone to the reboiler zone. A predetermined liquid level is maintained in the reboiler zone by a control valve, 55, mounted in line 50 for the withdrawal of liquid. This valve is responsive to a level sensing device, 56, such as a manometer, which detects the reboiler liquid level.

In operation, premixed ethylene-glycol degraded polyethylene terephthalate waste, methanol, and zinc acetate are heated to 190° to 230°C. and then pumped to the vessel through line 42. The feed contains a sufficient amount of methanol to maintain a stoichiometric excess in the reaction zone, generally a weight ratio of at least 2 to 1, preferably at least 3 to 1, methanol to glycol-degraded waste. The feed contains about 200 ppm by weight of zinc acetate catalyst, based on weight of the glycol-degraded waste.

Pressure of the reaction zone is maintained substantially at the partial vapor pressure of methanol in the reaction zone to prevent any significant quantity of methanol feed from evaporating. The pressure is controlled by a valve in the purge line as discussed hereinbefore. In the reaction zone dimethyl terephthalate and ethylene glycol are formed by ester exchange between methanol and the glycol-degraded waste.

The liquid reaction solution slowly passes downward through the reaction zone, by passage through spaces between the perforated trays. At a point in the lower region of the reaction zone where the ester exchange has reached the desired degree of completion (e.g., when about 90% or more of the terephthalate values in the feed solution have been converted to dimethyl terephthalate), the solution comes into contact with a catalyst sequestering agent, typically phosphoric acid, introduced through line 46. At this point the catalyst is deactivated and methanol can be removed from the solution without significantly reversing the ester exchange reaction.

After the catalyst has been deactivated, the hot solution is withdrawn from the reaction zone and introduced to the reboiler zone through line 52. The reboiler zone is heated to a temperature sufficiently higher than that of the reaction zone to evolve methanol vapor having a pressure high enough to overcome resistance to upward vapor flow presented by the liquid head, superatmospheric pressure, and trays in the ester exchange column. Methanol vapors continuously pass through the barrier plate and bubble upward through liquid in the reaction zone, continuously agitating the liquid, and into the vapor space at the top of the vessel. Ascending vapors, as they pass through the reaction zone, collect beneath the trays, 45, and are redispersed as bubbles by passing through the tray perforations.

Ethylene glycol and other vapors evolved in the reboiler also pass through the barrier plate but are condensed as they rise through the reaction zone. Condensation primarily occurs in the lower region of the reaction zone and does not affect the ester exchange dimethyl terephthalate yield to any significant extent.

Pressure in the vapor space at the top of the vessel is maintained substantially at the partial vapor pressure of methanol at the reaction zone temperature so that significant quantities of methanol are only evolved in the reboiler zone; i.e., methanol is evaporated after the ester exchange catalyst has been deactivated. Vapors at the top of the column, primarily methanol, exit the vessel through line 43, are condensed, and are returned to the vessel by line 44.

The reaction zone is typically maintained at 200°C. and at a pressure of about 500 to 550 psia, with liquids in the reboiler zone being heated to 220° to 230°C.

Under these conditions, and employing about a 60 minute holding time in the reaction zone and up to a 10 minute holding time in the reboiler zone, dimethyl terephthalate yields up to about 87% or more of the theoretical yield are obtained while reducing the methanol content in the solution by up to about 70% or more.

Hot solution withdrawn from the reboiler zone by line 50 contains dimethyl terephthalate, residual methanol, diethylene glycol, ethylene glycol, catalyst residues, solids introduced with the wastes, and small quantities of uncompletely reacted wastes and condensation by-products. Dimethyl terephthalate is conveniently recovered from the solution by, in sequence, distilling off the residual methanol, removing the solids using sedimentation, filtration or centrifugation techniques, distilling off the aliphatic components, and distilling off dimethyl terephthalate from the remaining solution. The process disclosed and claimed in copending, coassigned application Ser. No. 442,910 of R. M. Currie et al. filed herewith for Polyester Waste Recovery, incorporated herein by reference, can be used for recovery purposes.

The apparatus of this invention reduces the methanol feed requirements since it provides for internal methanol recycle, and conserves heat since the methanol is recycled at an elevated temperature. Moreover, the apparatus permits process flexibility in that it can accommodate waste containing various additives and is readily integrated in a continuous waste recovery operation. The process can be used to recover terephthalate values from textile or film wastes, as well as from polyester articles returned for recycle. For example, polyethylene terephthalate articles, such as used bottles, can be collected and transported to a central location where they can be glycol-degraded to serve as feed to the polyethylene terephthalate manufacturing process.

While the apparatus has been described in detail with respect to the conversion of polyester wastes, it will be understood that the apparatus may be equally useful in other processes to achieve internal recycle of at least a portion of the more volatile reactants, or solvents, present.

I claim:

1. Apparatus for conducting a continuous, catalyzed, reversible chemical reaction in the liquid state under pressure while maintaining internal recycle of the more volatile liquid present comprising:
   1. a closed reaction vessel with an upper reaction zone and a lower reboiler zone, said reaction zone having an entrance port for reactants and catalyst, and said reboiler zone having an exit port for reaction product;
   2. a perforated barrier plate mounted in the reaction vessel to separate said reaction zone from said reboiler zone;
   3. liquid level sensing means mounted in said reaction zone to detect the level of liquid reactants therein;
   4. a conduit by-passing the perforated barrier plate to transport liquid from said reaction zone to said reboiler zone;
   5. control means mounted in said by-pass conduit responsive to said reaction zone liquid level sensing means to maintain the reaction zone substantially filled with reactants in the liquid state;
   6. liquid level sensing means mounted in the reboiler zone to detect the level of liquid therein;
   7. a conduit connected to said exit port to remove liquid product from the reboiler zone, said conduit having mounted therein control means responsive to said reboiler liquid level sensing means, maintaining liquid in the reboiler zone at a predetermined level;
   8. heating means to maintain liquid in said reboiler zone at a higher temperature than in said reaction zone; and
   9. means to inject a catalyst sequestering agent into a lower region of said reaction zone.

2. Apparatus of claim 1 wherein perforated plates are mounted in the reaction zone to form bubbles from ascending vapors.

3. Apparatus of claim 1 including means to condense and recycle vapors collecting above the liquid reaction zone.

* * * * *